United States Patent [19]

Meilland, deceased

[11] Patent Number: Plant 6,598

[45] Date of Patent: Feb. 14, 1989

[54] ROSE PLANT—MEILONTIG VARIETY

[75] Inventor: Marie-Louise Meilland, deceased, late of Antibes, France, by Jean-Pierre Le Naour, legal representative

[73] Assignee: The Conard-Pyle Company, West Grove, Pa.

[21] Appl. No.: 60,305

[22] Filed: Jun. 10, 1987

[51] Int. Cl.[4] ..... A01H 5/00

[52] U.S. Cl. ..... Plt./1

[58] Field of Search ..... Plt./1

*Primary Examiner*—Robert E. Bagwill

*Attorney, Agent, or Firm*—Burns, Doane, Swecker & Mathis

[57] ABSTRACT

A new and distinct variety of shrub rose plant is provided which forms in moderation attractive single white blossoms. The variety exhibits an extremely rapid growth habit and forms arching canes which become horizontal as the plant matures. An excellent aptitude for rooting and growing on its own roots is exhibited. The new variety is well adapted for growing as a landscape planting.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) of the new variety was the Meiburenac variety which is sometimes known as the Swany variety (non-patented in the United States). The male parent (i.e., the pollen parent) of the new variety was the New Dawn variety U.S. Plant Pat. No. 1). The parentage of the new variety can be summarized as follows:

Meiburenac × New Dawn.

The seeds resulting from the above pollination were sown and 4 plantlets were obtained which were physically and biologically different from each other. Selective study resulted in the identification of a single plant of the new variety.

It was found that the new variety of shrub rose plant of the present invention possesses the following combination of characteristics:

(a) forms in moderation attractive single white blossoms,
(b) exhibits an extremely rapid growth habit,
(c) forms rambling arching canes which become horizontal as the plant matures,
(d) exhibits an excellent aptitude for rooting and growing on its own roots, and
(e) is particularly well suited for growing in the landscape.

The new variety meets the needs of the horticultural industry for all uses. It can be grown to advantage as an attractive ornamentation in parks, gardens, public areas, and residential landscapes. It is well suited for growing in large open spaces.

The characteristics of the new variety have been found to be homogeneous and stable and are strictly transmissible by asexual propagation from one generation to another.

The new variety has been named the Meilontig variety.

BRIEF DESCRIPTION OF THE PHOTOGRAPH

The accompanying photograph shows, as nearly true as it is reasonably possible to make the same in a color illustration of this character, typical specimens of plant parts of the new variety. The rose plants of the new variety described herein were grown outdoors during June on their own roots at Var, France.

DETAILED DESCRIPTION

Figures 1, 2, 3, 4, 5, 6, 7, 8, 9, 10, 11, 12, 13, 14, 15, 16:
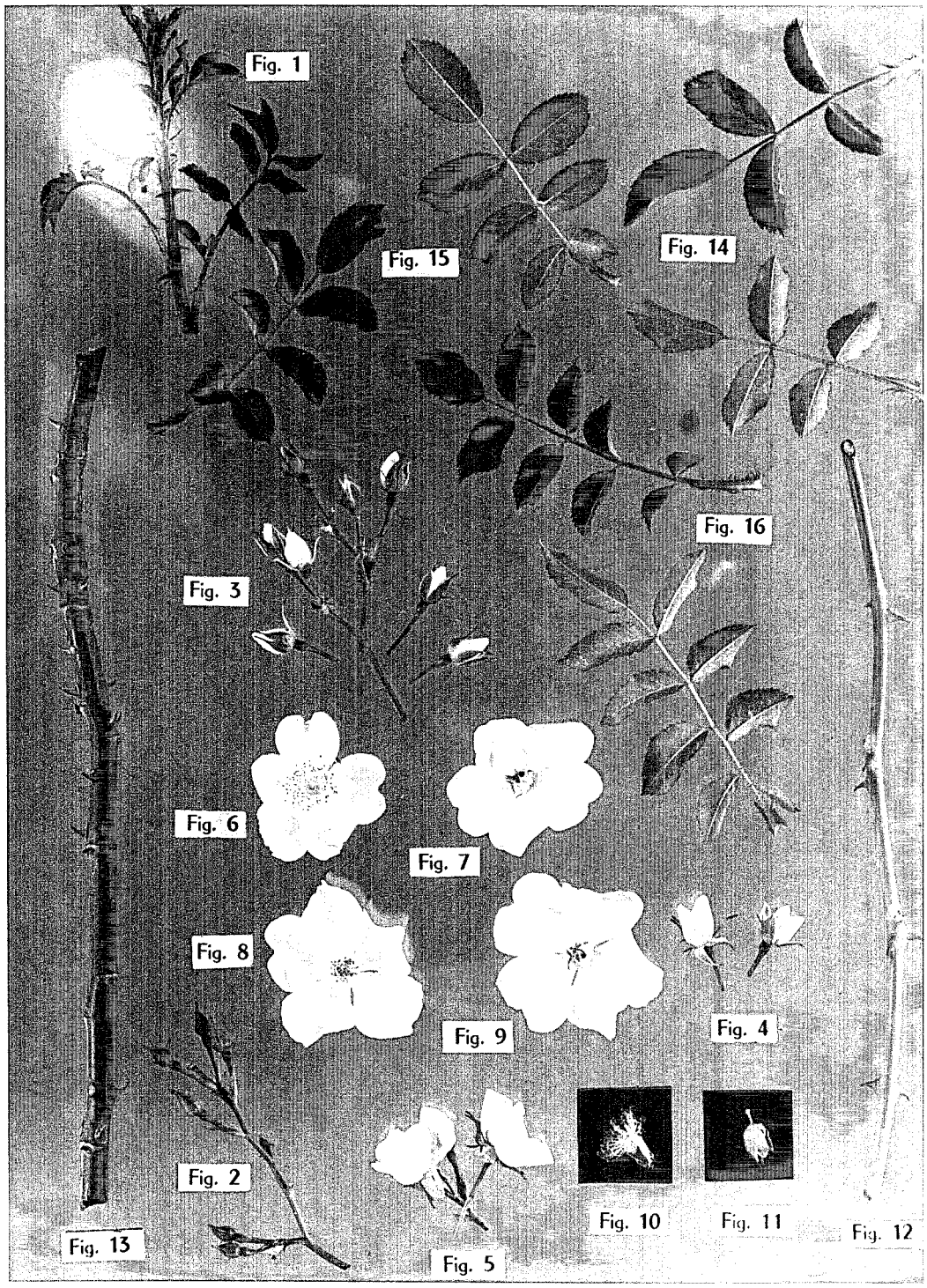
FIG. 1 illustrates a specimen of a young shoot.
FIG. 2 illustrates a specimen of floral buds before the opening of the sepals.
FIG. 3 illustrates a specimen of floral buds at the opening of the sepals.
FIG. 4 illustrates a specimen of a pair of floral buds as the petals open.
FIG. 5 illustrates a specimen of a pair of flowers in the course of opening.
FIG. 6 illustrates a specimen of a fully open flower—plan view—obverse.
FIG. 7 illustrates a specimen of a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a pair of leaves with five leaflets—upper surface (above figure identification) and under surface (below figure identification)
FIG. 15 illustrates a specimen of a leaf with seven leaflets—under surface.
FIG. 16 illustrates a specimen of a leaf with nine leaflets—upper surface.

The chart used in the identification of colors is that of The Royal Horticultural Society (R.H.S. Colour Chart). The description is based on specimens of the new variety during June while grown outdoors on their own roots at Var, France.

Class: Shrub.

Plant:

*Height.*—Approximately 100 to 150 cm. on average.

*Habit.*—Rambling arching canes become horizontal as plant matures.

Branches:

*Color.*—Young stems: Yellow-green Group 146D. Adult wood: Yellow-green Group 146B.

Leaves:

*Petioles.*—Upper surface: grooved, reddish-brown on young foliage, medium green on mature foliage. Under surface: medium green with several small thorns.

*Leaflets.*—Number: 3, 5, 7 (most often), and 9. Shape: Eliptical. Serration: Simple and regular. Texture: leathery. Overall appearance: Foliage is ample, dense and glossy. Color (young foliage): Upper surface: Yellow-green Group 144A, somewhat suffused with red. Under surface: Yellow-green Group 144B, somewhat suffused with red. Color (adult foliage): Upper surface: Yellow-green Group 146A. Under surface: Yellow-green Group 146B.

Inflorescence:

*Number of flowers.*—Approximately 5 to 10 blossoms per floral stem.

*Peduncle.*—Approximately 2.0 to 2.5 cm. in length.

*Buds.*—Shape: conical. Length: Approximately 1.0 cm. on average. Color: Upper surface: White Group 155A. Under surface: White Group 155A.

*Flower.*—Form: Single, basically flat with slightly cupped petals. Diameter: Approximately 6 to 7 cm. on average. Color (when opening begins): Upper surface: White Group 155A. Under surface: White Group 155A. Color (when partially open): Upper surface: White group 155A. Under surface: White Group 155A. Color (at end of opening): Upper surface: White Group 155A. Under surface: White Group 155A. Fragrance: None. Flower duration: Long. Petal form: Generally heart shaped. Petal number: Commonly 5. Stamen number: Approximately 98 to 105 on average. Anthers: Normal. Pistils: Approximately 10 on average.

Development:

*Blossoming.*—Moderate to low production of flowers.

I claim:

1. A new and distinct variety of shrub rose plant characterized by the following combination of characteristics:

(a) forms in moderation attractive single white blossoms, (b) exhibits an extremely rapid growth habit, (c) forms rambling arching canes which become horizontal as the plant matures, (d) exhibits an excellent aptitude for rooting and growing on its own roots, and (e) is particularly well suited for growing in the landscape;

substantially as herein shown and described together with the parts thereof.

* * * * *